United States Patent [19]
Pollard et al.

[11] Patent Number: 5,366,977
[45] Date of Patent: Nov. 22, 1994

[54] METHOD OF TREATING CYSTIC FIBROSIS USING 8-CYCLOPENTYL-1,3-DIPROPYLXANTHINE OR XANTHINE AMINO CONGENERS

[75] Inventors: Harvey B. Pollard, Potomac; Philip J. M. van Galen, Rockville; Kenneth A. Jacobson, Silver Spring, all of Md.

[73] Assignee: The United States of America, as represented by the Department of Health and Human Services, Washington, D.C.

[21] Appl. No.: 952,965

[22] Filed: Sep. 29, 1992

[51] Int. Cl.$^5$ .................... A61K 31/52; A61K 31/505
[52] U.S. Cl. ..................................... 514/263; 514/267
[58] Field of Search ......................... 514/263; 544/267

[56] References Cited

U.S. PATENT DOCUMENTS

| | | | |
|---|---|---|---|
| 4,769,377 | 9/1988 | Snyder | 514/263 |
| 4,772,607 | 9/1988 | Badger | 514/263 |
| 4,968,672 | 11/1990 | Jacobson | 514/46 |
| 5,032,593 | 7/1991 | Rzeszotarski | 514/267 |

FOREIGN PATENT DOCUMENTS

| | | | |
|---|---|---|---|
| 0001735 | 5/1979 | European Pat. Off. | C07D 473/06 |
| 0038784 | 10/1981 | European Pat. Off. | C07D 473/06 |
| 8602551 | 5/1986 | WIPO | A61K 31/415 |

OTHER PUBLICATIONS

Beach et al Chem Abstr. 118(3): 19932 of *Am. J. Physiol.* 263(3,Pt 2) F482–487 (Sep. 1992).
Alzheimer et al, *Neuroscience Let.* 99: 107–112 (1989).
Eidelman et al "A$_1$ adenosine-receptor antagonists" Proc. Natl. Acad. Sci. 89: 5562–5566 Jun. 1992.
Merck Manual, 14th ed., pp. 634–639, 1982.
Arispe et al., "Intrinsic anion channel activity of the recombinant first nucleotide binding fold domain of the cystic fibrosis transmembrane regulator protein," Proc. Natl. Acad. Sci. USA, 89: 1539–1543. Mar 1992.
Barrett et al., "Differing effects of apical and basolateral adenosine on colonic epithelial cell line T$_{84}$, " Am. J. Physiol. 256 (Cell Physiol. 25): C197–C203. 1989.
Baumgold et al., "Penetration of Adenosine Antagonists Into Mouse Brain As Determined By *Ex Vivo* Binding," Biochemical Pharmacology, 43(4): 889–894. 1992.
Behnke et al., "Differential Antagonism by 1,3-Dipropylxanthine-8-cyclopentylxanthine and 9-Chloro-2-(2-Furanyl)-5,6-Dihydro-2,4-Triazolo(1,5-c)quinazolin-5-imine . . . in Cardiomyocytes," Journal of Pharmacology and Experimental Therapeutics, 254(3): 1017–1023. 1990.
Böhm, et al., "Characterization of A$_1$ Adenosine Receptors in Atrial and Ventricular Myocardium From Diseased Human Hearts," Circulation Research, 65(5): 1201–1211. Nov. 1989.
Brackett et al., "Activities of Caffeine, Theophylline, and Enprofylline Analogs As Tracheal Relaxants," Biochemical Pharmacology, 39(12): 1897–1904. 1990.
Bruns et al., "Binding of the A$_1$-selective adenosine antagonist 8-cyclopentyl-1,3-dipropylxanthine to rat brain membranes," Naunyn-Schmiedberg's Arch. Pharmacol., 335: 59–63. 1987.
Drumm et al., "Chloride Conductance Expressed by ΔF508 and Other Mutant CFTRs in Xeinopus Oocytes," Science, 254: 1797–1799. Dec. 20, 1991.

(List continued on next page.)

Primary Examiner—Gregory Hook
Attorney, Agent, or Firm—Leydig, Voit & Mayer

[57] ABSTRACT

A method of treating cells having a reduced apical Cl$^-$ conductance, such as that characteristic of cystic fibrosis cells, by contacting cells having a reduced apical Cl$^-$ conductance with a therapeutically effective quantity of a compound that antagonizes the A$_1$-adenosine cell receptor and does not antagonize the A$_2$-adenosine cell receptor. Suitable compounds include 8-cyclopentyl-1,3-dipropylxanthine (CPX), xanthine amino congener (XAC), and therapeutically effective derivatives thereof.

14 Claims, 7 Drawing Sheets

OTHER PUBLICATIONS

Garritsen et al., "Chemical Modification of Adenosine $A_1$ Receptors," Biochemical Pharmacology, 40(4): 835–842. 1990.

Jacobson et al., "8–Substituted Xanthines as Antagonists at $A_1$- and $A_2$- Adenosine Receptors," Biochemical Pharmacology, 37(19): 3653–3661. 1988.

Jacobson et al., "Adenosine ($P_1$) and ATP ($P_2$) Receptors," Comprehensive Medicinal Chemistry, 3(Membranes and Receptors): 601–642. 1990.

Jacobson et al., "Novel Therapeutics Acting Via Purine Receptors," Biochemical Pharmacology, 41(10): 1399–1410. 1991.

Ji et al., "Characterization of Human Striatal $A_2$–Adenosine Receptors Using Radioligand Binding and Photoaffinity Labelling," Journal of Receptor Research, 12(2): 149–169. 1992.

Kellett et al., "Amelioration of glycerol–induced acute renal failure in the rat with 8–cyclopentyl–1,3–dipropylxanthine," Br. J. Pharmacol., 98: 1066–1074. 1989.

Kelley et al., "Endogenous Adenosine is an Autacoid Feedback Inhibitor of Chloride Transport in the Shark Rectal Gland," J. Clin. Invest., 88: 1933–1939. Dec. 1991.

Knowles et al., "A Pilot Study of Aerosolized Amiloride For The Treatment of Lung Disease In Cystic Fibrosis," The New England Journal of Medicine, 322(17): 1189–1194. Apr. 26, 1990.

Knowles et al., "Activation By Extracellular Nucleotides of Chloride Secretion In The Airway Epithelia of Patients With Cystic Fibrosis," The New England Journal of Medicine, 325(8): 533–538. Aug. 22, 1991.

Schepp et al., "Dual modulation by adenosine of gastrin release from canine g–cells in primary culture," Am. J. Physiol. 259 (Gastrointest. Liver Physiol. 22): G556–G563. 1990.

Snyder et al., Proc. Natl. Acad. Sci. USA, 78(5): 3260–3264. May 1981.

von der Leyen et al., "Effects of 1,3–dipropyl–8–cyclopentylxanthine (DPCPX), a highly selective andenosine receptor atangonist, on force of contraction in guinea–pig atrial and ventricular cardiac preparations," Nauyn–Schmiedeberg's Arch. Pharmacol., 340: 204–209. 1989.

2-thio-CPX

KW-3902

CPT, MW 248.3

METHOD OF TREATING CYSTIC FIBROSIS USING 8-CYCLOPENTYL-1,3-DIPROPYLXANTHINE OR XANTHINE AMINO CONGENERS

FIELD OF THE INVENTION

The present invention relates to a method of treating cells having a reduced apical Cl⁻ conductance, such as cystic fibrosis cells. Specifically, the present inventive method involves contacting cells having a reduced apical Cl⁻ conductance with a therapeutically effective quantity of a compound that antagonizes the $A_1$-adenosine cell receptor and does not antagonize the $A_2$-adenosine cell receptor.

BACKGROUND OF THE INVENTION

Cystic fibrosis (CF) is an inherited multi-system disorder that is characterized by an abnormality in exocrine gland function. More specifically, CF is caused by mutations in the cystic fibrosis transmembrane regulator (CFTR) gene. The mutations in the CFTR gene result in an abnormal potential difference across CF epithelia. The abnormality is due to a reduced cellular apical Cl⁻ conductance. Consequently, chloride and sodium transport across mucous membranes is abnormal. This abnormality is apparently responsible for pathophysiological changes in the respiratory system. Nearly all patients suffering from the disease develop chronic progressive disease of the respiratory system. Also, in the majority of cases, pancreatic dysfunction occurs, and hepatobiliary and genitourinary diseases are also frequent. The incidence of the disease among white Americans is between 1/1600 and 1/2000 live births. Among Afro-Americans, the incidence is much reduced—about 1/17,000 live births. Although survival of cystic fibrosis patients has improved in recent years, the median survival is still only about 20 years despite intensive supportive and prophylactic treatment.

Present efforts to combat the disease have focused on drugs that are capable of either activating the mutant CFTR gene product or causing additional secretion of Cl⁻ from affected cells, as well as gene therapy, wherein the anion conductance deficit is repaired by the introduction of a recombinant wild-type CFTR gene, i.e., a CFTR gene that lacks a mutation that results in the abnormality.

Encouraging clinical results have been reported recently for the use of aerosols containing either amiloride (Knowles et al., N. Engl. J. Med. 322: 1189–1194. 1990.) or a mixture of ATP and UTP (Knowles et al., N. Engl. J. Med. 325: 533–538. 1991.), which slow the accumulation of Cl⁻ in the epithelium of the trachea.

Other drugs that are purportedly useful in the treatment of CF have been described. For example, U.S. Pat. No. 4,866,072 describes the use of 9-ethyl-6,9-dihydro-4,6-dioxo-10-propyl-4H-pyrano(3,2-g)quinoline2,8-dicarboxylic acid or a pharmaceutically acceptable derivative thereof in the treatment of CF. U.S. Pat. No. 4,548,818 describes the use of a 3-alkylxanthine to treat chronic obstructive pulmonary disease (COPD). U.S. Pat. No. 5,032,593 describes the use of a 1,3-alkyl substituted 8-phenylxanthine or a pharmaceutically acceptable salt thereof in the treatment of bronchoconstriction. U.S. Pat. No. 5,096,916 describes the use of an imidazoline α-adrenergic blocking agent and vasodilator, such as tolazoline, in the treatment of COPD, including cystic fibrosis, chronic bronchitis and emphysema, or COPD in association with asthma.

Historically, theophylline has been administered to asthmatic and CF patients to enhance lung function. The mechanism of theophylline has been shown to involve both the inhibition of phosphodiesterase and the antagonism of adenosine receptors. Since theophylline acts at more than one site, it lacks specificity. In view of the fact that antagonism of the $A_1$ adenosine receptor, not inhibition of phosphodiesterase, has been shown to result in chloride efflux, such lack of specificity could result in undesired side effects. In addition, large doses of theophylline must be administered to achieve a beneficial effect, at the same time risking side effects from the high toxicity of the compound.

Other compounds that resemble theophylline in basic structure have been tested but have not been found to be useful in the treatment of cystic fibrosis. For example, IBMX (see FIG. 1A), which is structurally similar to theophylline, is nonspecific in activity and highly toxic and, therefore, lacks utility in the treatment of CF. Also ineffective in the activation of chloride efflux are the compounds 2-thio-CPX, KW-3902, and CPT (see FIG. 1B). Similarly, substitution of the propyl group at position $R_1$ or $R_3$ of CPX (see FIG. 1A) with a one-carbon group generates a compound that is ineffective in activating chloride efflux from CF cells. Clearly, minor structural differences have a significant, if not substantial, impact on the effectiveness of the compound in the treatment of CF.

A drug of high potency, low toxicity, and high specificity for the $A_1$ adenosine receptor, however, would be a highly desirable and promising therapeutic agent for the treatment of cells having a reduced apical Cl⁻ conductance, such as cystic fibrosis cells. Such a drug would not only find utility in the treatment of cystic fibrosis per se but would be therapeutically useful in the treatment of COPD in general.

It is an object of the present invention to provide such a method of treating cells having a reduced apical Cl⁻ conductance. It is another object of the present invention to provide a method of treating cystic fibrosis cells. It is yet another object of the present invention to provide a method of treating cystic fibrosis cells having a deletion involving phenylalanine at amino acid position 508 of the cystic fibrosis transmembrane regulator.

These and other objects and advantages of the present invention, as well as additional inventive features, will be apparent from the description of the invention provided herein.

BRIEF SUMMARY OF THE INVENTION

The present invention provides a method of treating cells having a reduced apical Cl⁻ conductance, such as cystic fibrosis cells. Specifically, the present inventive method involves contacting cells having a reduced apical Cl⁻ conductance with a therapeutically effective quantity of a compound that antagonizes the $A_1$-adenosine cell receptor and does not antagonize the $A_2$-adenosine cell receptor. In particular, the method involves contacting such cells with a compound such as 8-cyclopentyl-1,3-dipropylxanthine (CPX), xanthine amino congener (8-[4-[2-aminoethylaminocarbonylmethyloxy]-phenyl]-1,3-dipropylxanthine, XAC), or a therapeutically effective derivative thereof.

The compounds used in the present inventive method, which are known in the art, resemble theophylline in basic structure; however, they differ significantly in the substituents at the $R_1$, $R_3$, and $R_8$ positions. Given that minor structural differences in compounds that resemble theophylline have been shown to render the compounds ineffective or otherwise not useful in the treatment of CF, it was surprising to discover that CPX and XAC are effective in activating chloride efflux from CF cells. For example, CPX is twice as effective as theophylline at 1/30,000 the concentration in activating chloride efflux from CF cells without any accompanying toxicity.

BRIEF DESCRIPTION OF THE DRAWINGS

FIGS. 2-6 graphically describe various experiments involving specific $A_1$-adenosine antagonists (i.e., CPX and XAC), nonspecific $A_1$-adenosine antagonists (i.e., IBMX and theophylline), a phosphodiesterase inhibitor (i.e., rolipram), an exogenous adenosine agonist (i.e., 2-chloroadenosine), an enzyme that removes adenosine by converting it to inactive inosine (i.e., adenosine deaminase), and an adenylate cyclase activator (i.e., forskolin).

DETAILED DESCRIPTION OF THE PREFERRED EMBODIMENTS

The present invention provides a method of treating cells having a reduced apical $Cl^-$ conductance, such as cystic fibrosis cells. Specifically, the method involves contacting cells having a reduced apical $Cl^-$ conductance with a therapeutically effective quantity of a compound that antagonizes the $A_1$-adenosine cell receptor and does not antagonize the $A_2$-adenosine cell receptor. In particular, the method involves contacting such cells with a compound such as 8-cyclopentyl-1,3-dipropylxanthine (CPX), xanthine amino congener (8-[4-[2-aminoethylaminocarbonylmethyloxy]phenyl]-1,3-dipropylxanthine, XAC), or a therapeutically effective derivative thereof. CPX is a preferred compound in the context of the present invention because it is a potent low-toxicity drug that specifically activates $Cl^-$ efflux from CF cells.

The present inventive method has particular utility in the treatment of cystic fibrosis cells. The method is especially preferred in the treatment of cystic fibrosis cells that have a deletion involving phenylalanine at amino acid position 508 of the cystic fibrosis transmembrane regulator, in particular those cystic fibrosis cells found within a human patient.

Figure 1A:
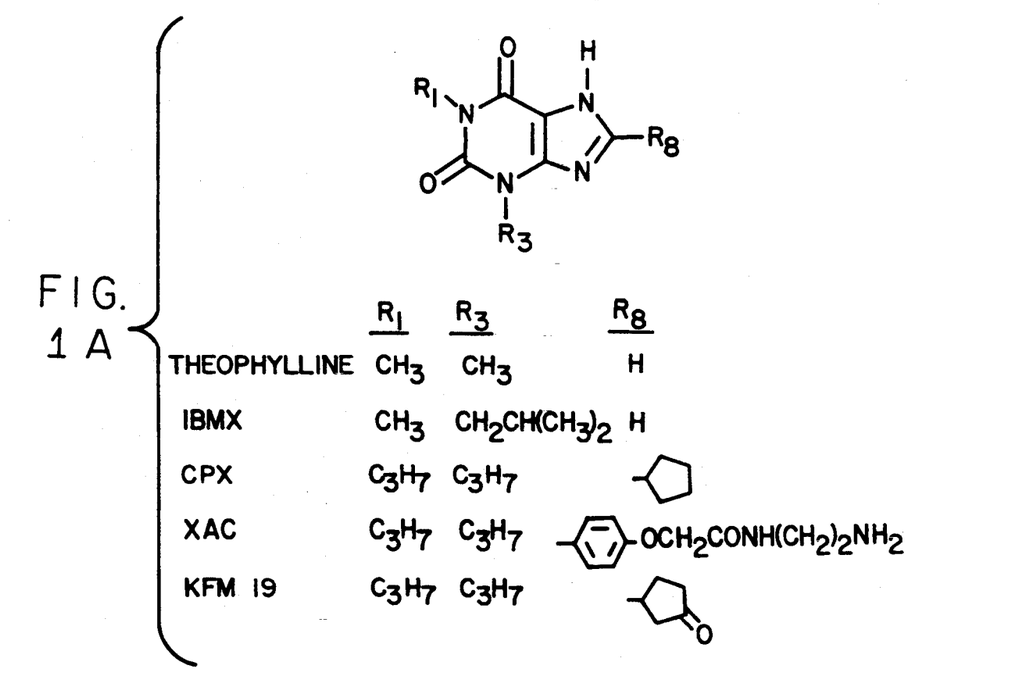
FIG. 1A is a drawing that shows the structures of a number of xanthine-analogue adenosine receptor antagonist drugs.
Figure 1B:
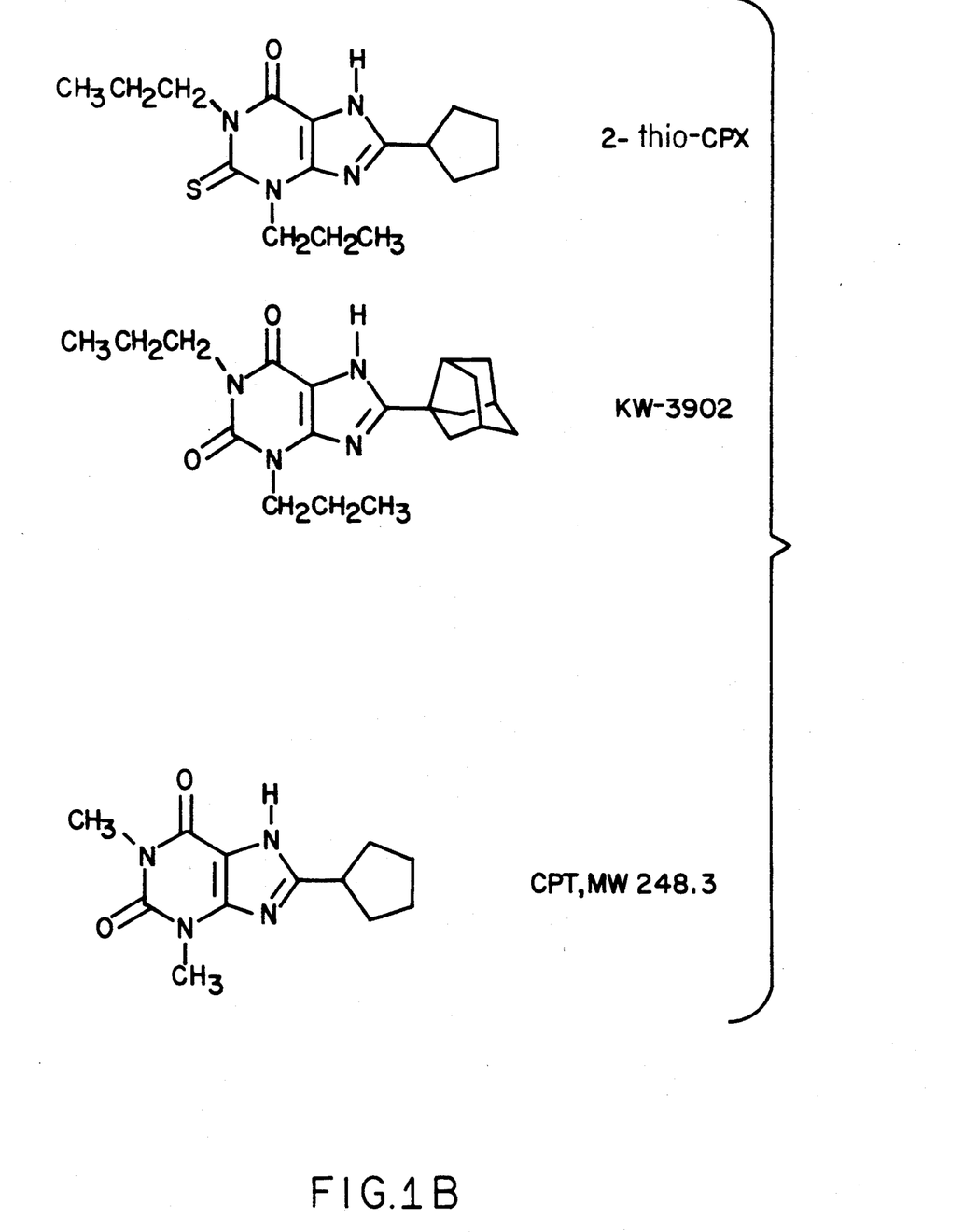
FIG. 1B is a drawing that shows the structures of several $A_1$ adenosine receptor antagonists that do not activate chloride efflux from CFPAC cells, which are pancreatic adenocarcinoma cells from a cystic fibrosis patient who is homozygous for the CFTR deletion of Phe-508.

The compound used in the present inventive method is preferably one that does not have phosphodiesterase activity. It is also preferred that the therapeutically effective quantity of the compound is nontoxic. Most preferably, the compound, itself, is nontoxic. Especially preferred compounds for use in the present inventive method are 8-cyclopentyl-1,3-dipropylxanthine (CPX) and xanthine amino congener (8-[4-[2-aminoethylaminocarbonylmethyloxy]phenyl]-1,3-dipropylxanthine, XAC). It is believed that the compound KFM 19 (see FIG. 1), which resembles CPX with the exception of an oxygen substituent on the cyclopentyl group, would also be useful in the present inventive method.

Alternatively, or additionally, a pharmaceutically acceptable derivative of CPX or XAC may be used in the present inventive method. It is desirable that such a derivative have equivalent therapeutic effectiveness in the context of the present inventive method of treatment.

The compound useful in the present inventive method may be administered by any suitable means. One skilled in the art will appreciate that many suitable methods of administering the compound to an animal in the context of the present invention, in particular a human, are available, and, although more than one route may be used to administer a particular compound, a particular route of administration may provide a more immediate and more effective reaction than another route.

The compound is preferably administered directly to the lung of a patient. Preferably, the compound is administered as a pharmaceutically acceptable aqueous solution. It is even more preferable that the compound be administered as a pharmaceutically acceptable aqueous solution containing from about 0.001 to about 0.01% w/w of the compound. A pharmaceutically acceptable aerosol is another preferred means of administration. The aerosol preferably contains from about 0.001 to about 0.01% w/w of the compound.

The compound also may be administered orally. In such a case, the compound will be generally administered in an amount of about 0.1 mg/kg body weight per day. Other routes of administration, such as intravenous and intraperitoneal administration, are also possible.

The compound should be administered such that a therapeutically effective concentration of the compound is in contact with the affected cells of the body. The dose administered to an animal, particularly a human, in the context of the present invention should be sufficient to effect a therapeutic response in the animal over a reasonable period of time. The dose will be determined by the strength of the particular compound employed and the condition of the animal, as well as the body weight of the animal to be treated. The size of the dose also will be determined by the existence, nature, and extent of any adverse side effects that might accompany the administration of a particular compound and the particular route of administration employed with a particular patient. In general, the compounds of the present invention are therapeutically effective at low doses. The effective dosage range is from about 30 nM to about 100 nM. Accordingly, the compounds will be generally administered in low doses.

The compound may be administered in a pharmaceutically acceptable carrier. Pharmaceutically acceptable carriers are well-known to those who are skilled in the art. The choice of carrier will be determined in part by the particular compound, as well as by the particular method used to administer the composition. Accordingly, there is a wide variety of suitable formulations of the pharmaceutical composition of the present invention.

Formulations suitable for oral administration include (a) liquid solutions, such as an effective amount of the compound dissolved in diluents, such as water or saline, (b) capsules, sachets or tablets, each containing a predetermined amount of the active ingredient, as solids or granules, (c) suspensions in an appropriate liquid, and (d) suitable emulsions. Tablet forms may include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels and the like containing, in addition to the active ingredient, such carriers as are known in the art.

Formulations suitable for administration by inhalation include aerosol formulations placed into pressurized acceptable propellants, such as dichlorodifluoromethane, propane, nitrogen, and the like. The active agent may be aerosolized with suitable excipients.

Formulations suitable for intravenous and intraperitoneal administration, for example, include aqueous and nonaqueous, isotonic sterile injection solutions, which can contain anti-oxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carriers for example, water, for injections, immediately prior to use. Extemporaneous injection solutions and suspensions can be prepared for sterile powders, granules, and tablets of the kind previously described.

The desirable extent of the induction of $Cl^-$ efflux from cells will depend on the particular condition or disease being treated, as well as the stability of the patient and possible side effects. In proper doses and with suitable administration of certain compounds, the present invention provides for a wide range of activation of the rate of chloride ion efflux, e.g., from little activation to essentially full activation.

The present invention is expected to be effective in the treatment of all conditions, including diseases, that may be characterized by a reduced cellular apical $Cl^-$ conductance. In particular, the present invention is expected to have utility in the treatment of chronic obstructive pulmonary diseases, in particular cystic fibrosis.

The following examples serve to further illustrate the present invention and are not intended to limit the scope of the invention.

EXAMPLE 1

This example describes the culture of CFPAC cells which are utilized in succeeding examples.

CFPAC cells are pancreatic adenocarcinoma cells from a CF patient, who is homozygous for the most common CFTR mutation, i.e., deletion of Phe-508 (Schoumacher et al., PNAS 87: 4012–4016. 1990.). CFPAC cells and CFTR-transfected CFPAC cells (CFPAC-4.7 CFTR) were obtained from R. Frizzell at the University of Alabama. The cells were split and seeded at low density on 24-well COSTAR plates in medium composed of Eagle's minimal essential medium with Dulbecco's modifications (DMEM), supplemented with 10% (vol/vol) heat-inactivated fetal calf serum, $1 \times 10^5$ units/ml penicillin, 100 mg/liter streptomycin, and 1% (wt/vol) glutamine. After 5 hours, the medium was replaced and attached cells were allowed to reach confluency during a period of 48 hours at 37° C. in 5% $CO_2$/95% air.

EXAMPLE 2

This example describes the measurement of chloride efflux from the cells of Example 1.

Before each experiment, cells were loaded with $^{36}Cl^-$ as follows. Confluent cells were washed four times in bicarbonate-free DMEM. Then, after aspirating the last wash, 250 μl of DMEM and 25 μl (approximately $1.4 \times 10^8$ cpm) of $^{36}Cl^-$ (Amersham) were added to each well. The plates of cells were then incubated at 37° C. for two hours in a $CO_2$-free incubator. The plates were then moved to 25° C., and drugs were added at various concentrations and times. After incubating, the cells were washed four times in 500 μl of an ice-cold wash medium composed of 150 mM sodium-gluconate and 10 mM Hepes (pH 7.4). At the end of the wash step, 500 μl of flux medium at 21° C. was added, and sampling was initiated by collecting 50 μl aliquots from each well at 0, 1, 2, 3, 5, 7, and 10 minutes. The flux medium consisted of 150 mM sodium gluconate, 1.5 mM potassium gluconate, 10 mM sodium Hepes (pH=7.4), 100 μM bumetanide to inhibit the cotransporter, and different drugs, e.g., $A_1$-adenosine antagonists and activators of cAMP synthesis, as required and described in subsequent examples. The osmolarity was 310 mOsm. At the end of each flux experiment, 20 μl of 50% trichloroacetic acid was added to a final concentration of 5% to obtain a measure of remaining radioactivity. Samples were mixed with 1.5 ml of Cytoscint fluid and assayed for two minutes on a Beckman LS9000 scintillation counter with windows at maximum width.

EXAMPLE 3

This example describes the treatment of cells in accordance with the present invention.

The cells of Example 1 were treated with drugs in accordance with the procedure of Example 2 as follows: forskolin (4 μM for 5 minutes), isobutylmethylxanthine (IBMX; 40 μM for 5 minutes), xanthine amino congener (XAC) or 8-cyclopentyl-1,3-dipropylxanthine (CPX) (various concentrations for 15 minutes), 2-chloroadenosine (100 μM for 30 minutes), and adenosine deaminase (2 units/ml for 30 minutes). Data from the scintillation counter were transferred by Data Module to a computer for analysis.

EXAMPLE 4

This example describes the effects of the drugs tested on the activation of chloride efflux from CF cells as set forth in Example 3.

Figure 2:
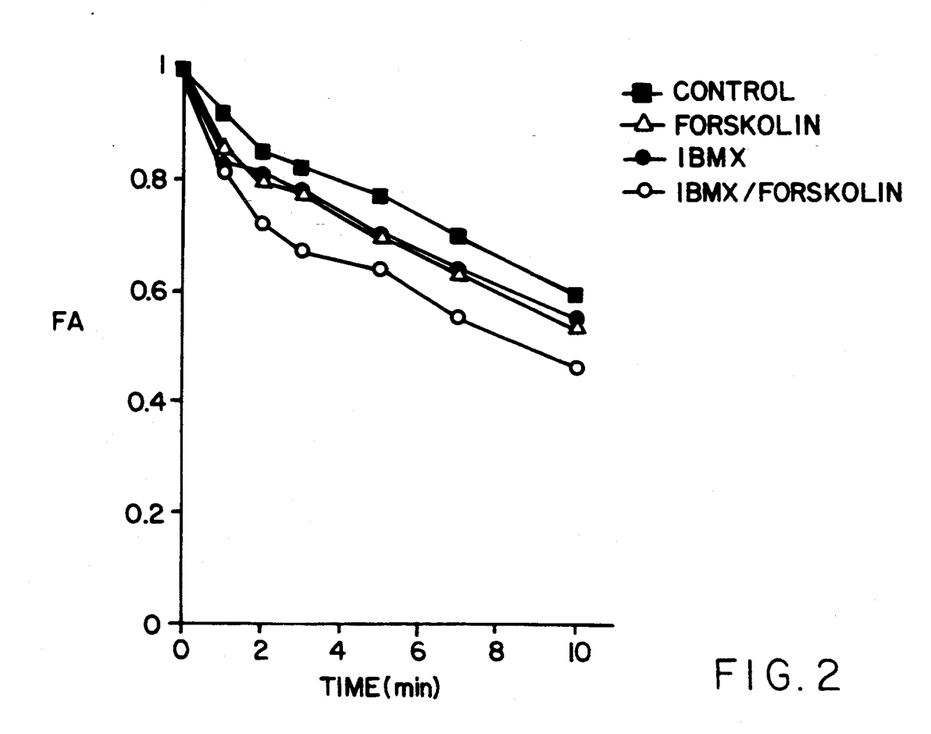
FIG. 2 is a graph of time (minutes) versus the fraction of total $^{36}Cl^-$ remaining in CFPAC cells at particular points in time. The effects of isobutylmethylxanthine (IBMX, ●), forskolin (Δ), and IBMX and forskolin combined (○) on chloride efflux from CFPAC cells in comparison to control cells (■) are shown.

The exposure of CFPAC cells to either IBMX (40 μM) or forskolin (4 μM) alone only modestly affected chloride efflux. However, exposure of the cells to a combination of the two drugs substantially increased the rate of chloride efflux by about 75% over control cells. These results are shown in FIG. 2. The action of IBMX is known to include not only inhibition of phosphodiesterase (Montague et al., Biochem. J. 122: 115–119. 1989.) but also antagonist activity on adenosine receptors (Snyder et al., PNAS 78: 3260–3264. 1981.).

The selective phosphodiesterase inhibitor rolipram (Schneider et al., In: Purines in Cellular Signaling: Targets for New Drugs. Springer-Verlag, N.Y. pp. 303–308.) did not affect chloride efflux in CFPAC cells. This suggests that antagonism of the $A_1$ adenosine receptor is the basis for chloride efflux.

Figure 3A:
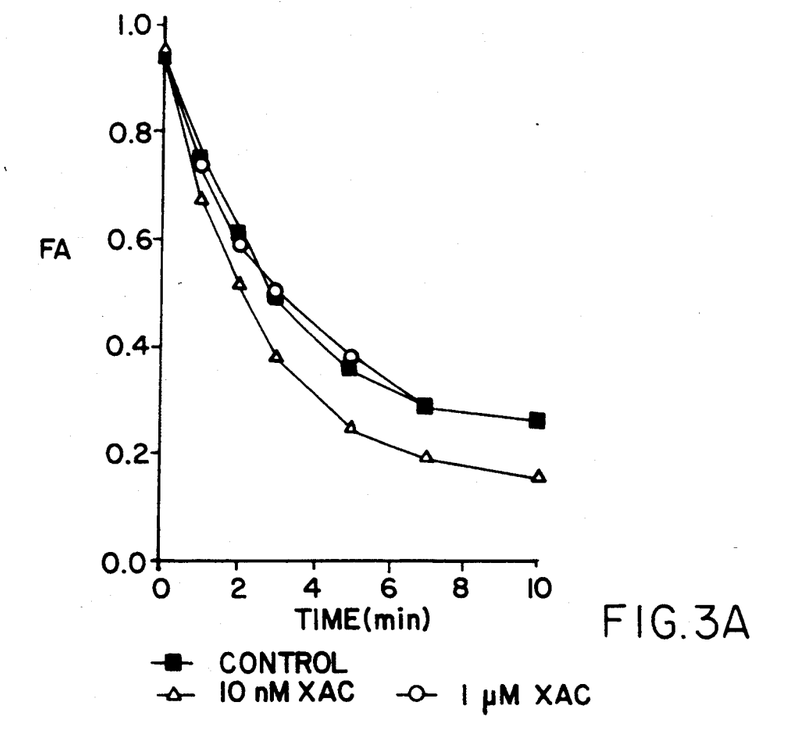
FIG. 3A is a graph of time (minutes) versus the fraction of $^{36}Cl^-$ remaining in CFPAC cells during an XAC efflux experiment. The effects of 10 nM XAC (Δ) and 1 μM XAC (○) in comparison to control cells (■) are shown.
Figure 3B:
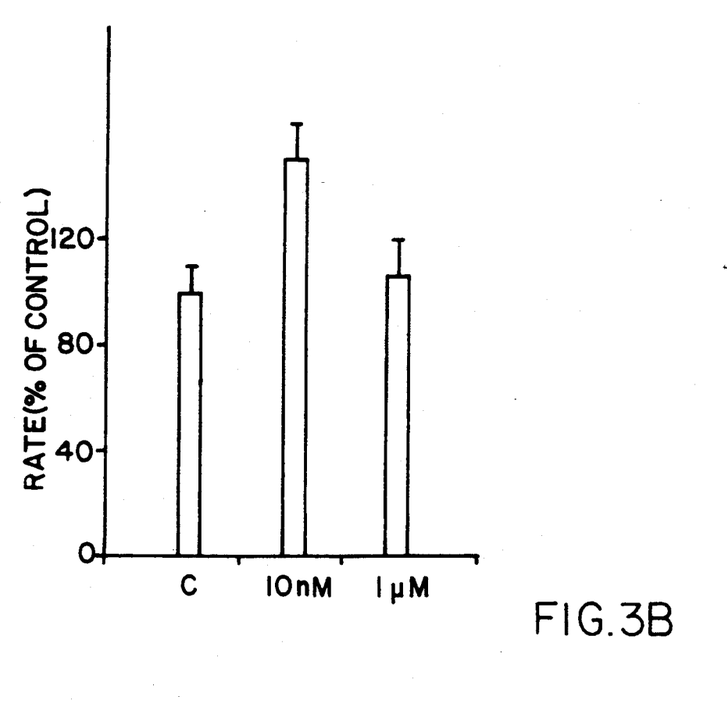
FIG. 3B is a bar graph of the relative rates of $^{36}Cl^-$ efflux (% of control cells) from CFPAC cells treated with zero, 10 nM, and 1 μM XAC. The rate was calculated from a curve fit to a first-order exponential function. The error bars show the SEM for four experiments.

XAC was found to be effective at low concentrations in evoking chloride efflux as shown in FIG. 3A. FIG. 3B summarizes the relative rate constants for the chloride efflux evoked by XAC at two concentrations in comparison with control cells. From these data, it is apparent that 10 nM XAC increases the rate of $^{36}Cl^-$ efflux from CFPAC cells by around 50%. At higher concentrations of XAC, i.e., $\geq 1$ μM, however, the chloride efflux rate returned to the control rate. The loss of activity at higher concentrations is believed to reflect either nonspecific activity or action on the $A_2$ adenosine receptor in addition to the $A_1$ adenosine receptor.

Figure 4A:
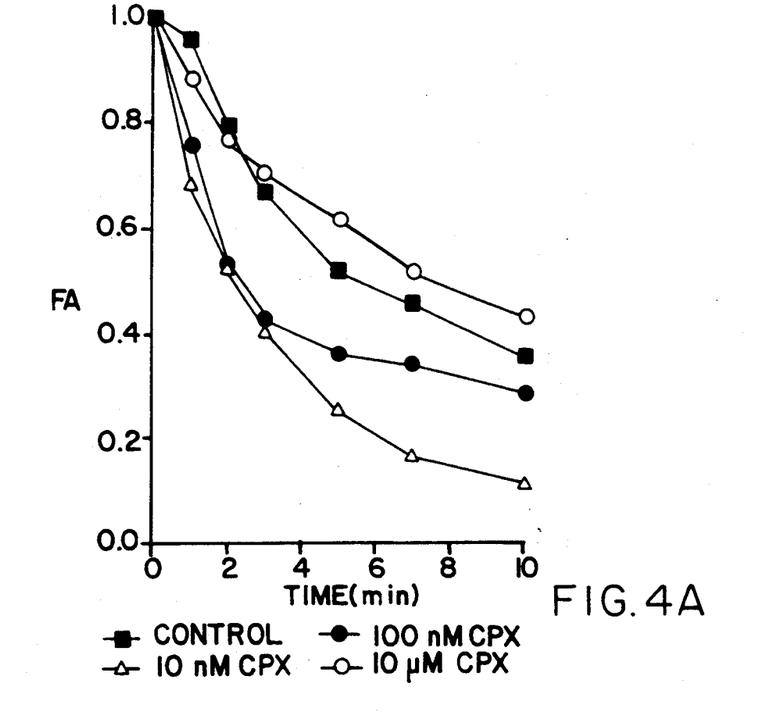
FIG. 4A is a graph of time (minutes) versus the fraction of $^{36}Cl^-$ remaining in CFPAC cells during a CPX efflux experiment. The effects of 10 nM (Δ), 100 nM (●), and 10 μM (○) CPX in comparison to control cells (■) are shown. The data were obtained in four experiments.
Figure 4B:
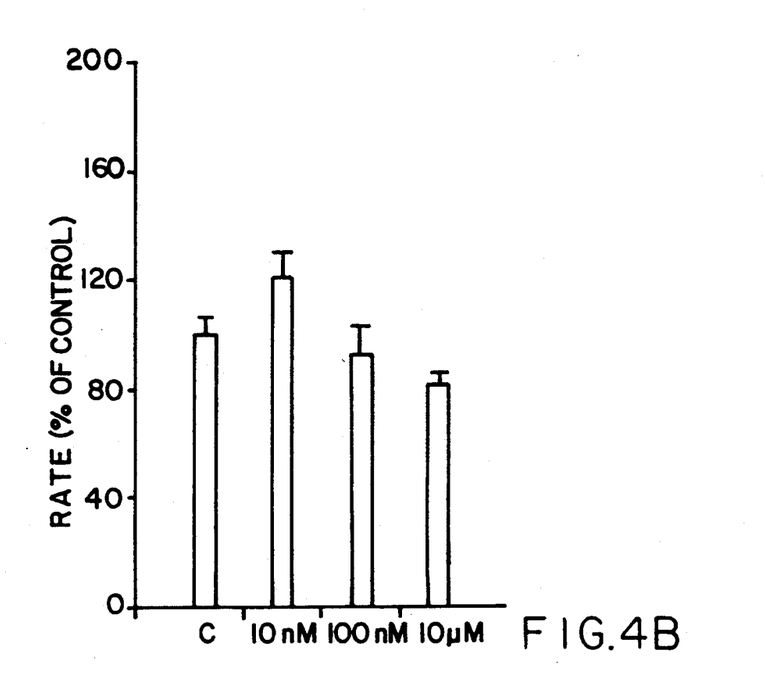
FIG. 4B is a bar graph of the relative rate of $^{36}Cl^-$ efflux (% of control cells) from CFPAC cells treated with zero, 10 nM, 100 nM, and 10 μM CPX. The rates constants were evaluated from a fit of the efflux data of FIG. 4A to a first-order rate equation. The error bars are those for the calculation of the efflux rates in FIG. 4A.

CPX, which is known to be somewhat more potent and more selective than XAC for human $A_1$ adenosine receptors (Ji et al., J. Recept. Res. 12: 149–169. 1992.; von der Leyen et al., Naunyn Schmiedeberg's Arch. Pharmakol. 340: 204–209. 1989.; Jacobson, In: Comprehensive Medicinal Chemistry, Vol. 3: 601–642. 1990.) was found to cause a profound activation of $^{36}Cl^-$ efflux at a concentration of 10 nM (FIG. 4A). Like XAC, CPX became less effective at higher concentrations. Eventually, CPX, at a concentration of 10 μM, reduced the rate of $^{36}Cl^-$ below that of the control rate (FIG. 4B).

In contrast with the results obtained with CPX and XAC on CFPAC cells, tests of XAC and CPX on the colon carcinoma cell lines HT-29 and T84, both of which contain the wild-type CFTR gene, and CFTR-transfected CFPAC cells did not result in activation of chloride efflux.

EXAMPLE 5

This example demonstrates the effects of a potent adenosine agonist and an adenosine deaminase on XAC activation of chloride efflux.

Figure 5A:
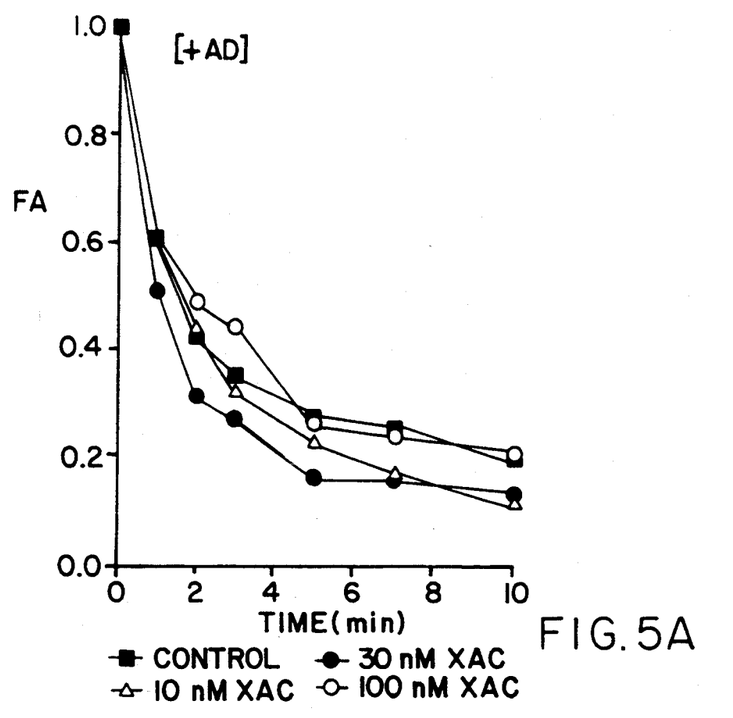
FIG. 5A is a graph of time (minutes) versus the fraction of $^{36}Cl^-$ remaining in CFPAC cells during an XAC efflux experiment. The cells were pretreated with adenosine deaminase. The effect of adenosine deaminase on the activity of CFPAC cells treated with 10 nM (Δ), 30 nM (●), and 100 nM (○) XAC in comparison to control cells (■) is shown.
Figure 5B:
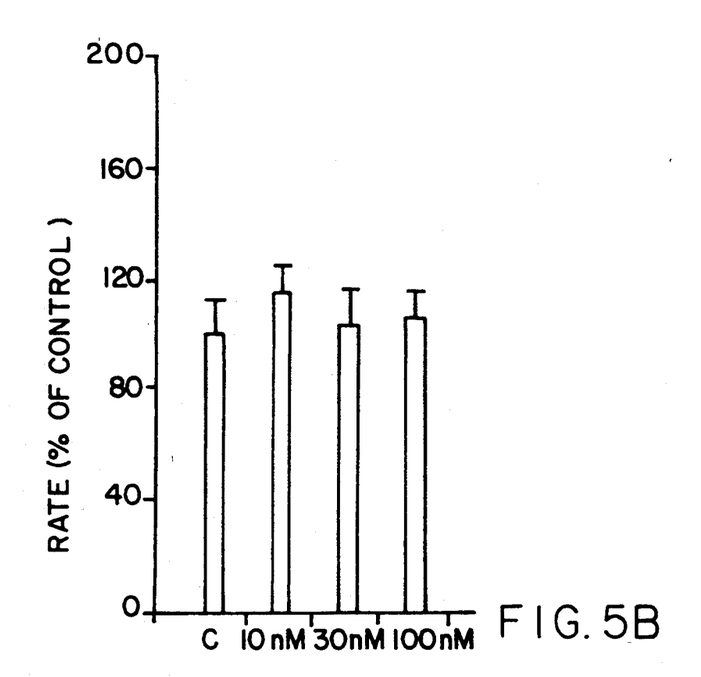
FIG. 5B is a bar graph of the relative rate of $^{36}Cl^-$ efflux (% of control cells) from CFPAC cells pretreated with adenosine deaminase and then treated with zero, 10 nM, 30 nM, and 100 nM XAC. The rate constants were calculated from the fit of the efflux data of FIG. 5A to a first-order rate equation.
Figure 5C:
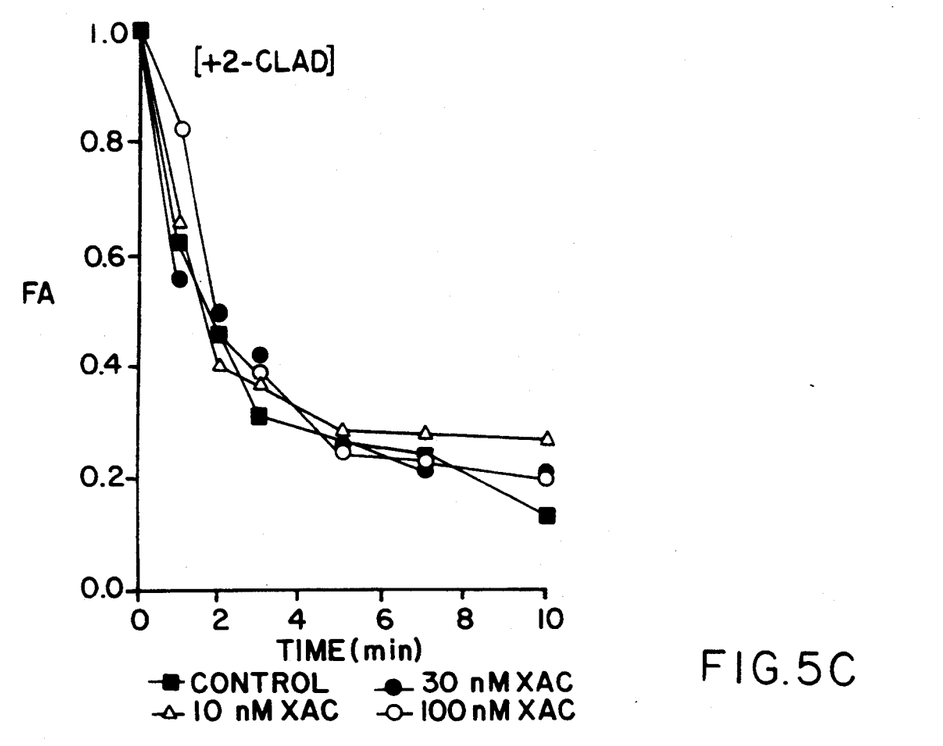
FIG. 5C is a graph of time (minutes) versus the fraction of $^{36}Cl^-$ remaining in CFPAC cells during an XAC efflux experiment. The cells were pretreated with 2-chloroadenosine. The effect of 2-chloroadenosine on the activity of cells treated with 10 nM (Δ), 30 nM (●), and 100 nM (○) XAC in comparison to control (■) cells is shown.
Figure 5D:
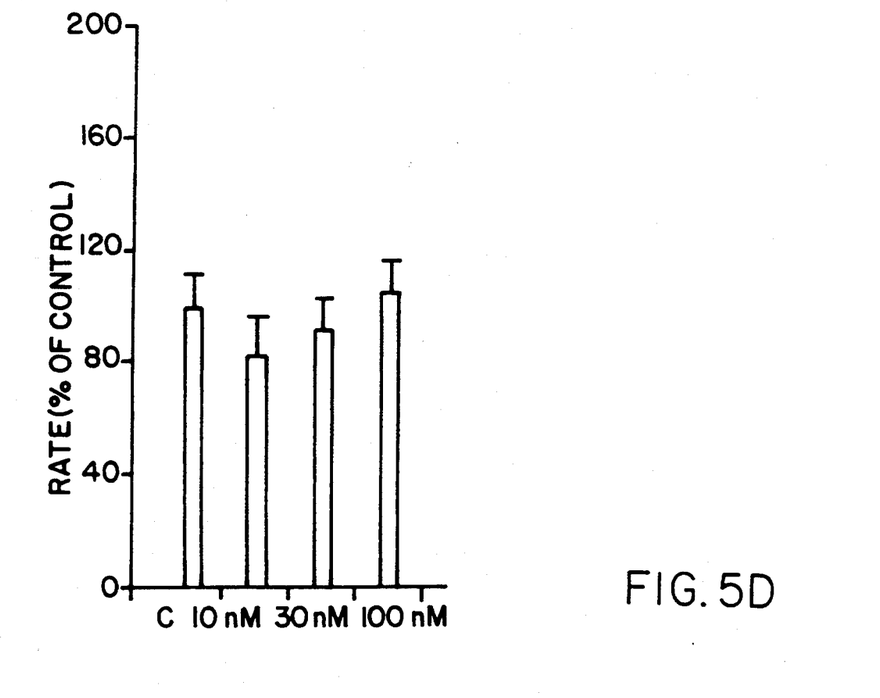
FIG. 5D is a bar graph of the relative rate of $^{36}Cl^-$ efflux (% of control cells) from CFPAC cells pretreated with 2-chloroadenosine and then treated with zero, 10 nM, 30 nM, and 100 nM XAC. The rate constants were calculated from the fit of the efflux data of FIG. 5C to a first-order rate equation.

The actions of the potent adenosine agonist 2-chloroadenosine (Jacobson, supra) and adenosine deaminase on XAC activation of chloride efflux were evaluated. Adenosine deaminase (see FIG. 5A) permitted only modest increases in the efflux rate upon further addition of XAC. Adenosine deaminase (see FIG. 5B) also suppressed efflux rates at higher XAC concentrations. Ten μM 2-chloroadenosine inhibited the action of XAC on chloride efflux from CFPAC cells (see FIGS. 5C and 5D). However, the highest dose level of XAC (300 μM) still reduced efflux rates to below control levels, despite the presence of 10 μM 2-chloroadenosine.

EXAMPLE 6

This example demonstrates the superior effectiveness of a comparatively low concentration of CPX over IBMX, theophylline, forskolin, and rolipram.

Figure 6:
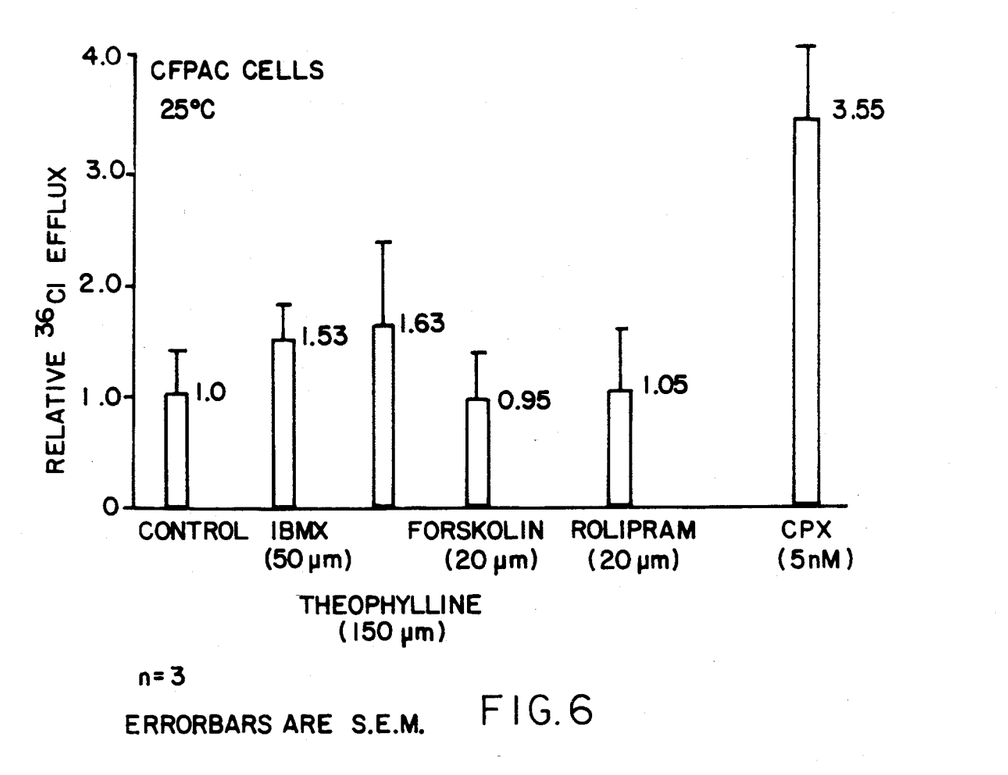
FIG. 6 is a bar graph of $^{36}Cl^-$ efflux (% of control cells) from CFPAC cells treated with 5 nM CPX, 50 μM IBMX, 150 μM theophylline, 20 μM forskolin, and 20 μM rolipram. The error bars show the SEM for three experiments.

The action of CPX (5 nM) was compared to that of IBMX (50 μM), theophylline (150 μM), forskolin (20 μM), and rolipram (20 μM). CPX was observed to activate chloride efflux from CFPAC cells more effectively than the other compounds and to do so at a much reduced level (see FIG. 6). For example, a 30,000-fold higher concentration of theophylline, i.e., 150 μM, which is toxic and not therapeutic for asthma, produced only a marginal effect, whereas a 30,000-fold lower concentration of CPX significantly activated chloride efflux from CFPAC cells.

The results of these examples indicate that it is possible to activate chloride efflux from CF cells by using a selective $A_1$ adenosine receptor antagonist, such as CPX or XAC. The specificity of these compounds for CF cells is illustrated by the fact that neither XAC nor CPX have discernible effects on chloride efflux from the colon carcinoma cell lines HT-29 and T84, both of which possess the wild-type CFTR message. Furthermore, CPX has no effect on CFTR-transfected CFPAC cells. The potential therapeutic advantages of a drug that is able to activate chloride efflux from CF cells specifically are appreciable, given that such drug action would tend to be less encumbered by unwanted side effects from unaffected tissues.

All of the publications identified herein are hereby incorporated by reference in their entireties.

While the invention has been described with an emphasis upon preferred embodiments, it will be obvious to those of ordinary skill in the art that variations in the preferred method can be used and that it is intended that the invention can be practiced otherwise than as specifically described herein. Accordingly, this invention includes all modifications encompassed within the spirit and scope of the invention as defined by the following claims.

What is claimed is:

1. A method of treating cystic fibrosis in a mammal in need of such treatment, which method comprises administering a therapeutically effective amount to said mammal of 8-cyclopentyl-1,3-dipropylxanthine or xanthine amino congener.

2. The method of claim 1, wherein said mammal is a human.

3. The method of claim 2, wherein said compound is 8-cyclopentyl-1,3-dipropylxanthine.

4. The method of claim 3, wherein said cystic fibrosis is characterized by the existence of cystic fibrosis cells in said human having a deletion involving phenylalanine at amino acid position 508 of the cystic fibrosis transmembrane regulator.

5. The method of claim 3, wherein said compound is administered directly to the lung of said human.

6. The method of claim 5, wherein said compound is administered as a pharmaceutically acceptable aqueous solution containing from about 0.001 to about 0.01% w/w of said compound.

7. The method of claim 5, wherein said compound is administered as a pharmaceutically acceptable aerosol containing from about 0.001 to about 0.01% w/w of said compound.

8. The method of claim 3, wherein said compound is orally administered in an amount of about 0.1 mg/kg body weight per day.

9. The method of claim 2, wherein said compound is xanthine amino congener.

10. The method of claim 9, wherein said cystic fibrosis is characterized by the existence of cystic fibrosis cells in said human having a deletion involving phenylalanine at amino acid position 508 of the cystic fibrosis transmembrane regulator.

11. The method of claim 9, wherein said compound is administered directly to the lung of said human.

12. The method of claim 11, wherein said compound is administered as a pharmaceutically acceptable aqueous solution containing from about 0.001 to about 0.01% w/w of said compound.

13. The method of claim 11, wherein said compound is administered as a pharmaceutically acceptable aerosol containing from about 0.001 to about 0.01% w/w of said compound.

14. The method of claim 9, wherein said compound is orally administered in an amount of about 0.1 mg/kg body weight per day.

* * * * *

UNITED STATES PATENT AND TRADEMARK OFFICE
CERTIFICATE OF CORRECTION

PATENT NO. : 5,366,977
DATED : November 22, 1994
INVENTOR(S) : Harvey B. Pollard, Philip J. M. Van Galen,
Kenneth A. Jacobson and Z. Ioav Cabantchik It is certified that error appears in the above-indentified patent and that said Letters Patent is hereby corrected as shown below:

On the title page: Item [75] Inventors:

After "all of Md". insert --Z. Ioav Cabantchik, Jerusalem, Israel --.

Signed and Sealed this

Sixteenth Day of May, 1995

Attest:

BRUCE LEHMAN

Attesting Officer

Commissioner of Patents and Trademarks